(12) United States Patent
Al-Ali et al.

(10) Patent No.: US 7,280,858 B2
(45) Date of Patent: Oct. 9, 2007

(54) PULSE OXIMETRY SENSOR

(75) Inventors: Ammar Al-Ali, Tustin, CA (US); Mohamed Kheir Diab, Mission Viejo, CA (US); Ronald Coverston, Portola Hills, CA (US); Garrick Maurer, Newport Beach, CA (US); John Schmidt, Lake Forest, CA (US); Chris Schulz, Rocklin, CA (US)

(73) Assignee: Masimo Corporation, Irvine, CA (US)

( * ) Notice: Subject to any disclaimer, the term of this patent is extended or adjusted under 35 U.S.C. 154(b) by 268 days.

(21) Appl. No.: 11/029,009

(22) Filed: Jan. 4, 2005

(65) Prior Publication Data

US 2005/0197550 A1 Sep. 8, 2005

Related U.S. Application Data

(60) Provisional application No. 60/534,331, filed on Jan. 5, 2004.

(51) Int. Cl.
*A61B 5/00* (2006.01)

(52) U.S. Cl. ........................ 600/323; 600/344

(58) Field of Classification Search ............... 600/309, 600/310, 322, 323, 344
See application file for complete search history.

(56) References Cited

U.S. PATENT DOCUMENTS

| | | | |
|---|---|---|---|
| 4,510,938 A * | 4/1985 | Jobsis et al. ................ 600/344 |
| 4,960,128 A | 10/1990 | Gordon et al. |
| 5,163,438 A | 11/1992 | Gordon et al. |
| 5,217,013 A * | 6/1993 | Lewis et al. ................ 600/342 |
| 5,226,417 A * | 7/1993 | Swedlow et al. ........... 600/336 |
| 5,337,744 A | 8/1994 | Branigan |
| 5,431,170 A | 7/1995 | Mathews |
| 5,452,717 A | 9/1995 | Branigan et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,590,649 A | 1/1997 | Caro et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |

(Continued)

*Primary Examiner*—Eric F Winakur
(74) *Attorney, Agent, or Firm*—Knobbe, Martens, Olson & Bear LLP

(57) ABSTRACT

A pulse oximetry sensor has an emitter adapted to transmit optical radiation of at least two wavelengths into a tissue site and a detector adapted to receive optical radiation from the emitter after tissue site absorption. A tape assembly is adapted to attach the emitter and detector to the tissue site. A flexible housing is disposed around and optically shields the detector.

22 Claims, 10 Drawing Sheets

U.S. PATENT DOCUMENTS

| | | | |
|---|---|---|---|
| 5,830,136 A * | 11/1998 | Delonzor et al. | 600/323 |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,112,107 A * | 8/2000 | Hannula | 600/310 |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,236,872 B1 | 5/2001 | Diab et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,334,065 B1 | 12/2001 | Al-Ali et al. | |
| 6,349,228 B1 | 2/2002 | Kiani et al. | |
| 6,360,114 B1 | 3/2002 | Diab et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,515,273 B2 | 2/2003 | Al-Ali | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Diab et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,697,656 B1 | 2/2004 | Al-Ali | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,725,075 B2 | 4/2004 | Al-Ali | |
| 6,745,060 B2 | 6/2004 | Diab et al. | |
| 6,760,607 B2 | 7/2004 | Al-Ali | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 2002/0016536 A1 * | 2/2002 | Benni | 600/323 |
| 2002/0165440 A1 * | 11/2002 | Mason et al. | 600/344 |

* cited by examiner

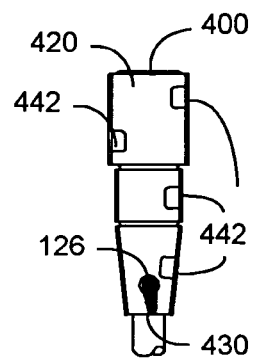
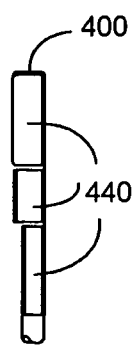
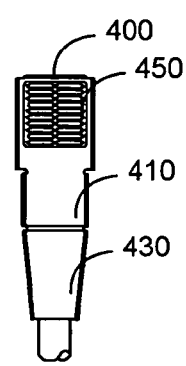
FIG. 4C  FIG. 4D  FIG. 4E
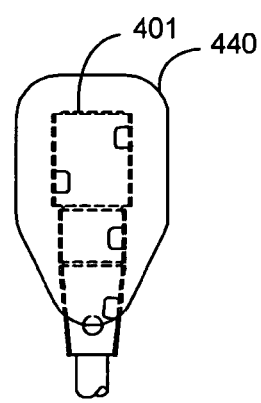
FIG. 4F

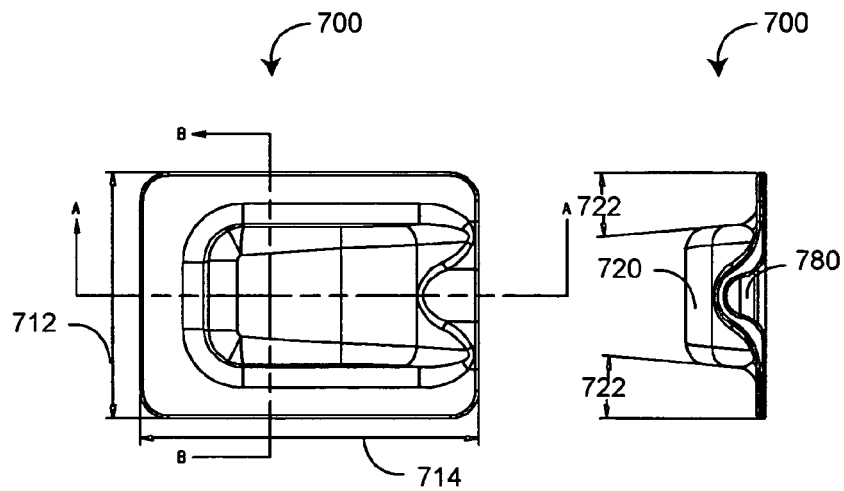
FIG. 7C        FIG. 7D
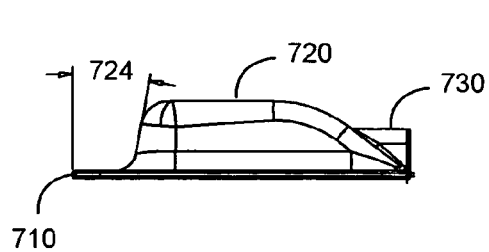    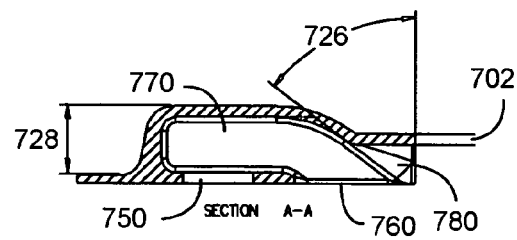
FIG. 7E        FIG. 7F
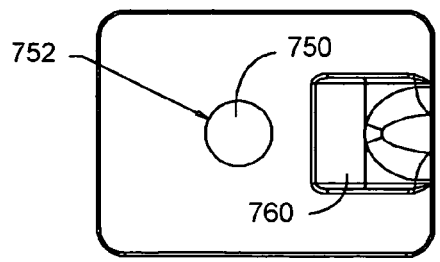    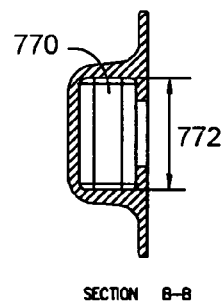
FIG. 7G        FIG. 7H

PULSE OXIMETRY SENSOR

CROSS-REFERENCE TO RELATED APPLICATIONS

This application relates to and claims the benefit of prior U.S. Provisional Patent Application No. 60/534,331 entitled Pulse Oximetry Sensor, filed Jan. 05, 2004 and incorporated by reference herein.

BACKGROUND OF THE INVENTION

Pulse oximetry is a widely accepted noninvasive procedure for measuring the oxygen saturation level of arterial blood, an indicator of a person's oxygen supply. Early detection of low blood oxygen level is critical in the medical field, for example in critical care and surgical applications, because an insufficient supply of oxygen can result in brain damage and death in a matter of minutes. A pulse oximetry system consists of a sensor applied to a patient, a monitor, and a patient cable connecting the sensor and the monitor. The sensor is attached to a tissue site, such as an adult patient's finger. The sensor has an emitter configured with both red and infrared LEDs that, for finger attachment, project light through the fingernail and into the blood vessels and capillaries underneath. A detector is positioned at the finger tip opposite the fingernail so as to detect the LED emitted light as it emerges from the finger tissues. In general, the emitter is adapted to transmit optical radiation of at least two wavelengths into a tissue site, and the detector is adapted to receive optical radiation from the emitter after absorption by pulsatile blood flowing within the tissue site.

SUMMARY OF THE INVENTION

There are various noise sources for a sensor including electromagnetic interference (EMI), ambient light and piped light. Light that illuminates the detector without propagating through the tissue site, such as ambient light and piped light, is unwanted optical noise that corrupts the desired sensor signal. Ambient light is transmitted to the detector from external light sources, i.e. light sources other than the emitter. Piped light is stray light from the emitter that is transmitted around a tissue site along a light conductive surface, such as a reflective inner surface of face stock material, directly to the detector. A pulse oximetry sensor advantageously provides EMI shielding and optical shielding, including multiple barriers to ambient light and piped light.

One aspect of a pulse oximetry sensor comprises an emitter adapted to transmit optical radiation of at least two wavelengths into a tissue site and a detector adapted to receive optical radiation from the emitter after tissue site absorption. A tape assembly is adapted to attach the emitter and detector to the tissue site. A flexible housing is disposed around and optically shields the detector.

Another aspect of a pulse oximetry sensor comprises a detector adapted to receive optical radiation from an emitter after absorption by pulsatile blood flowing within a tissue site. A shielded detector assembly has an EMI shield disposed around the detector. A housing assembly has a flexible housing disposed around the shielded detector assembly. A tape assembly is folded around the housing assembly and is adapted to attach the detector and emitter to the tissue site.

A further aspect of a pulse oximetry sensor is a method providing an emitter adapted to transmit optical radiation of at least two wavelengths into a tissue site and a detector adapted to receive optical radiation from the emitter after absorption by pulsatile blood flowing within the tissue site. The emitter and detector are incorporated within a cable assembly adapted to provide electrical communications between the emitter and detector and a monitor. The detector is EMI shielded so as to reduce electromagnetic noise, and the EMI shielded detector is optically shielded with an opaque, flexible housing so as to reduce optical noise from ambient and piped light. The cable assembly is disposed within a tape assembly adapted to attach the emitter and detector to a tissue site.

BRIEF DESCRIPTION OF THE DRAWINGS

FIGS. 4A-F are unassembled bottom, unfolded bottom, folded top, folded side, folded bottom and light barrier covered top views, respectively, of a shielded detector assembly;

FIGS. 7A-H are top perspective, bottom perspective, top, back, side, side cross sectional, bottom, and back cross sectional views, respectively, of a housing.

DETAILED DESCRIPTION OF THE PREFERRED EMBODIMENTS

Figure 1A:
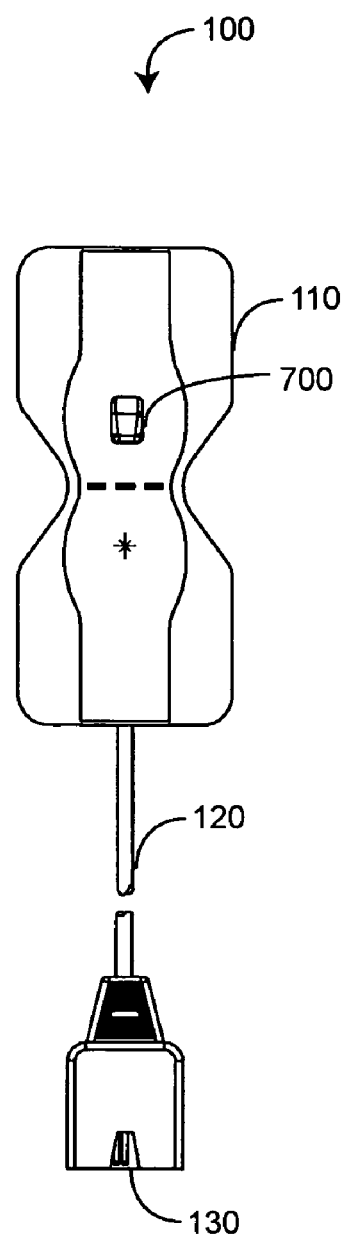
FIGS. 1A-C are assembled top plan, assembled perspective and packaged perspective views, respectively, of a pulse oximetry sensor.
Figure 1B:
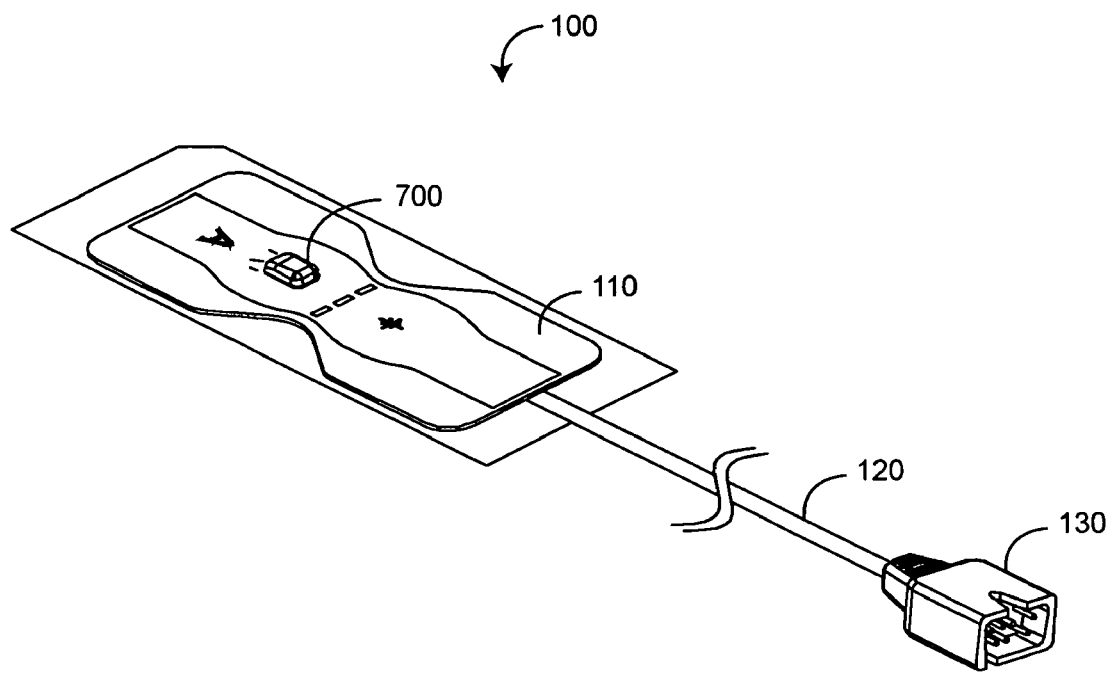
Figure 1C:
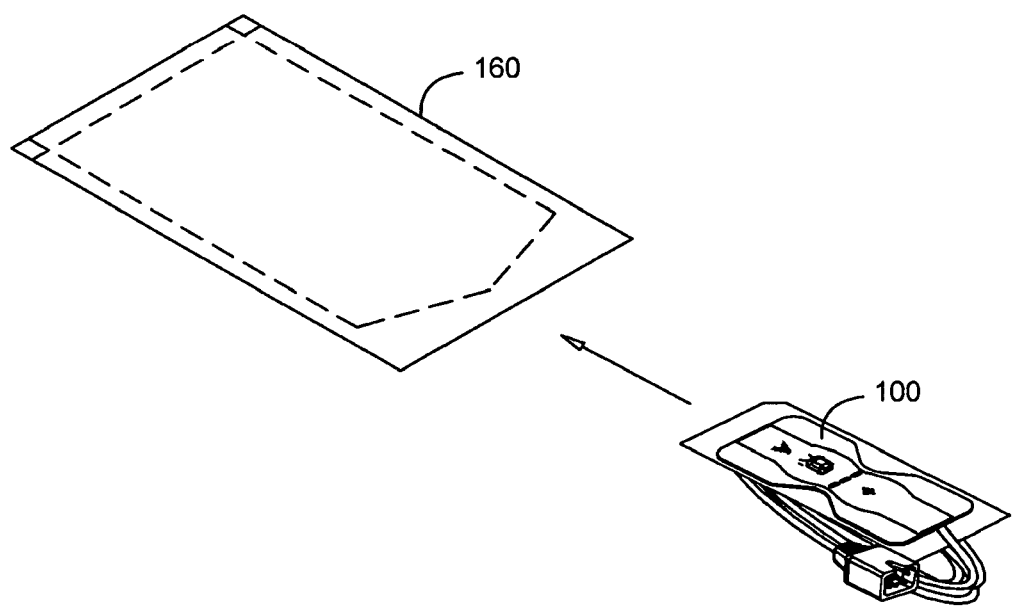
Figure 2:
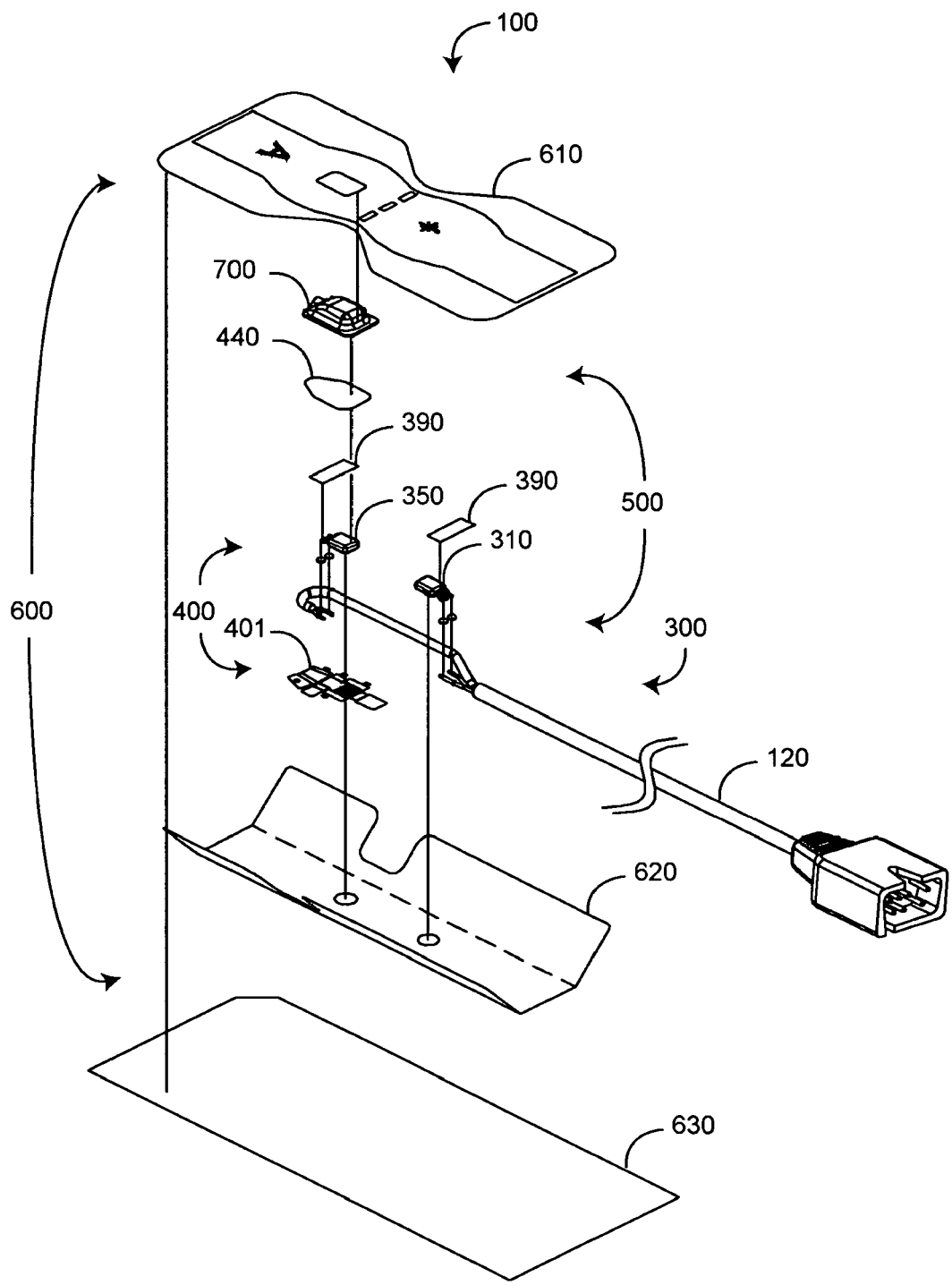
FIG. 2 is an exploded perspective view of a pulse oximetry sensor.

FIGS. 1A-C illustrate a pulse oximetry sensor 100 having a body 110, a cable 120 and a connector 130. The body 110 is configured to wrap around a fingertip and incorporates an emitter 310 (FIG. 2) and a detector 350 (FIG. 2) that provide physiological measurements responsive to a patient's blood oxygen saturation, as described above. The body 110 also incorporates a flexible housing 700 configured to enclose a shielded detector assembly 400 (FIG. 2). Advantageously, the flexible housing 700 optically shields the detector 350 (FIG. 2), blocking ambient and piped light. The cable 120 provides electrical communication between the emitter 310 (FIG. 2) and detector 350 (FIG. 2) and the connector 130. The connector 130 is adapted to a patient cable, which electrically and mechanically connects the sensor 100 to a monitor (not shown).

FIG. 2 further illustrates a pulse oximetry sensor 100 having a cable assembly 300, a shielded detector assembly 400, a housing assembly 500, a tape assembly 600 and a flexible housing 700. The cable assembly 300 has the cable 120, the emitter 310, the shielded detector assembly 400 and insulating tape 390, as described in detail with respect to FIGS. 3A-D. The shielded detector assembly 400 has the detector 350, an electromagnetic interference (EMI) shield 401 and a light barrier 440, as described in detail with respect to FIGS. 4A-F. The housing assembly 500 has the cable assembly 300 and the flexible housing 700, as described in detail with respect to FIGS. 5A-B. The tape assembly 600 has a face tape 610, a trifold wrap 620 and a release liner 630, as described in detail with respect to FIGS. 6A-D. The flexible housing 700 is described in detail with respect to FIGS. 7A-H.

Figure 3A:
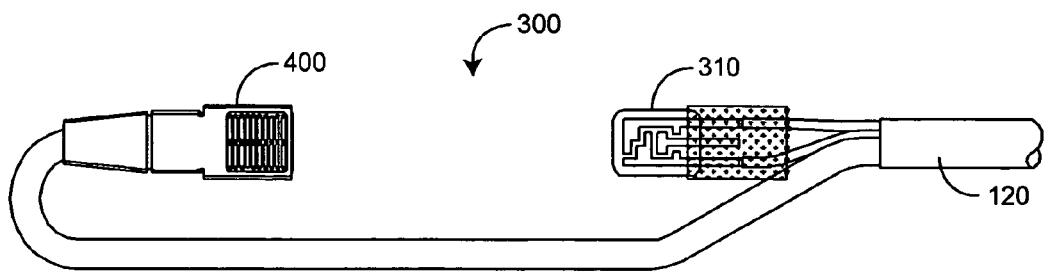
FIGS. 3A-D are shielded bottom, untaped top, untaped side and taped bottom views, respectively, of a cable assembly.
Figure 3B:
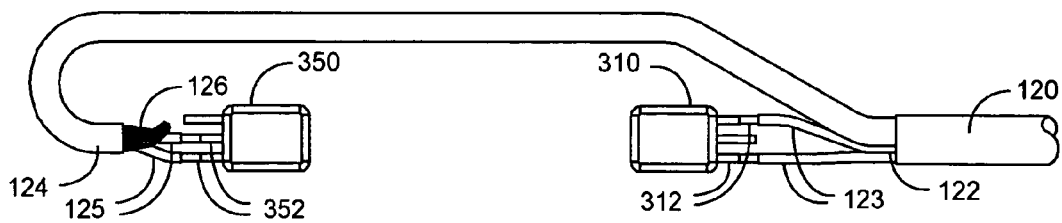
Figure 3C:
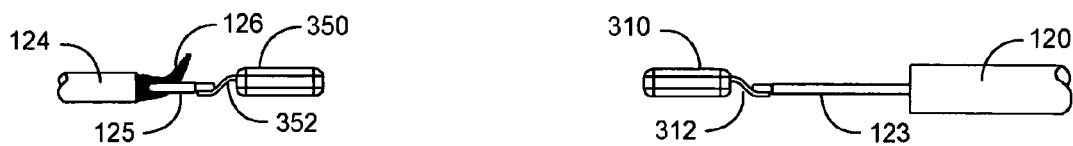
Figure 3D:
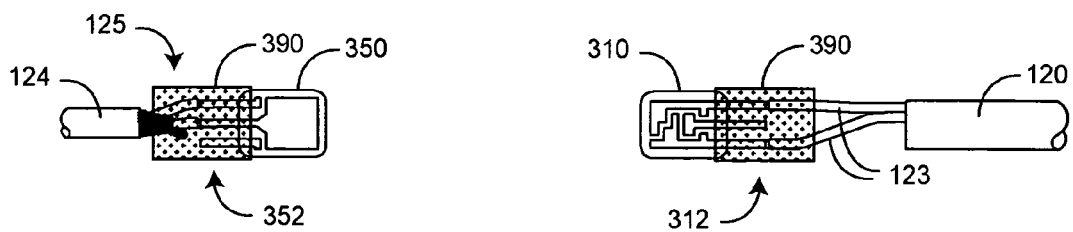

FIGS. 3A-D illustrate a cable assembly 300 having an emitter 310, a shielded detector assembly 400 and a cable 120. The detector 350 is incorporated within the shielded detector assembly 400. The cable 120 has an emitter portion 122 and a detector portion 124. A pair of emitter wires 123 extend from the emitter portion 122 and are soldered to corresponding emitter leads 312. A pair of detector wires 125 extend from the detector portion 124 and are soldered to corresponding detector leads 352. A cable shield 126 also extends from the detector portion 124 and is dressed for attachment to the EMI shield 401 (FIGS. 4A-B), as described below. As shown in FIG. 3D, insulating tape 390 is wrapped around the emitter wires 123 and emitter leads 312 at the emitter portion 122 and wrapped around the detector wires 125 and detector leads 352 at the detector portion 124.

FIGS. 4A-F illustrate a shielded detector assembly 400 having a detector 350, insulating tape 390 and an EMI shield 401. The EMI shield 401 has a front portion 410, a foldable back portion 420 and a cable portion 430. The front portion 410 is disposed between the back 420 and the cable 430 portions. A conductive grid 450 is disposed on the front portion 410. Foldable sides 440 extend from the side edges of the front portion 410 and the cable portion 430. Tabs 442 extend from some of the foldable sides 440. An aperture 432 is defined in the cable portion 430.

Figure 4A:
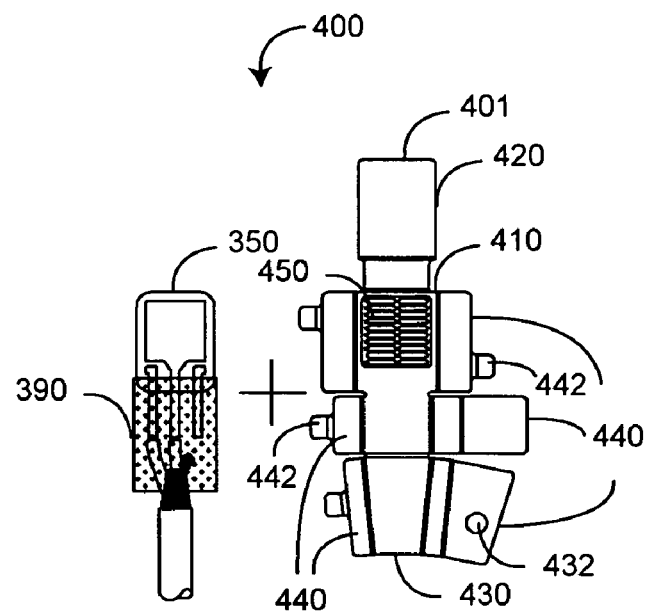
Figure 4B:
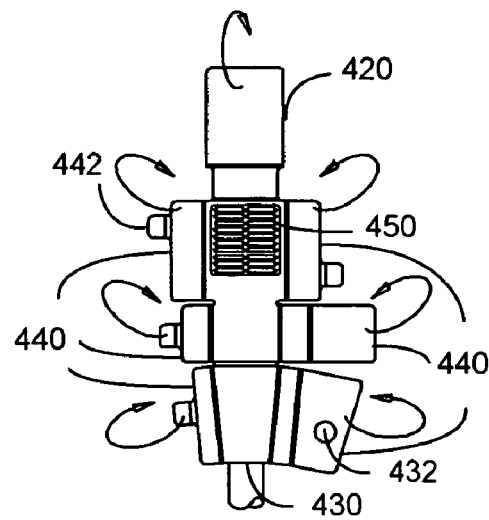

As shown in FIG. 4A, the detector 350 is placed on the inside of the EMI shield 401 so that the light sensitive areas of the detector 350 are proximate the grid 450. As shown in FIG. 4B, the back portion 420 and the sides 440 are folded back to cover the detector 350. As shown in FIGS. 4C-E, the tabs 442 secure the sides 440 and the back 420 in a closed position. The EMI shield 401 reduces electromagnetic interference at the detector 350. The grid 450 allows light from the emitter 410 that is attenuated by tissue to pass through to the detector 350. The cable shield 126 is placed through the aperture 432 and soldered or otherwise electrically connected to the cable portion 430 of the EMI shield 401. Any excess cable shield 126 is trimmed. As shown in FIG. 4F, a light barrier 440 is placed over the back of the EMI shield 401. In one embodiment, the light barrier 440 is a metal foil, such as aluminum.

Figure 5A:
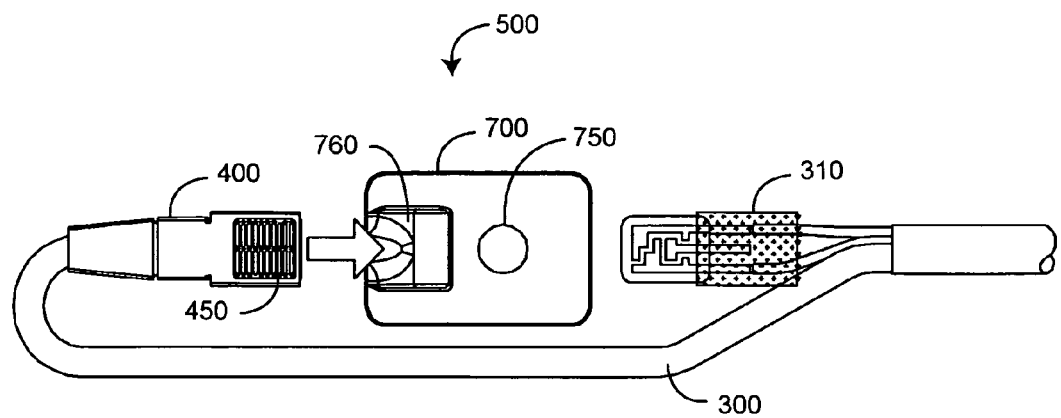
FIGS. 5A-B are unassembled and assembled bottom plan views, respectively, of a housing assembly.
Figure 5B:
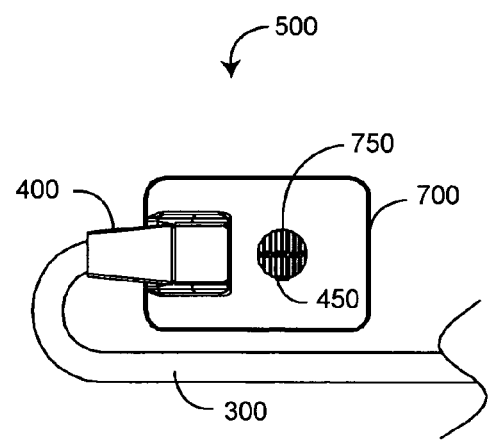

FIGS. 5A-B illustrate a housing assembly 500 having a cable assembly 300 attached to a flexible housing 700. The cable assembly 300 has an emitter 310 and the shielded detector assembly 400, as described above with respect to FIGS. 3A-D and FIGS. 4A-F, respectively. The housing 700 has an aperture 750 and an opening 760. The shielded detector assembly 400 is inserted into the housing 700 through the opening 760 and secured within a pocket 770 (FIG. 7F) so that the grid 450 is aligned with the aperture 750. The aperture 750 allows emitted light to pass to the detector 350 (FIG. 2) via the grid 450.

Figure 6A:
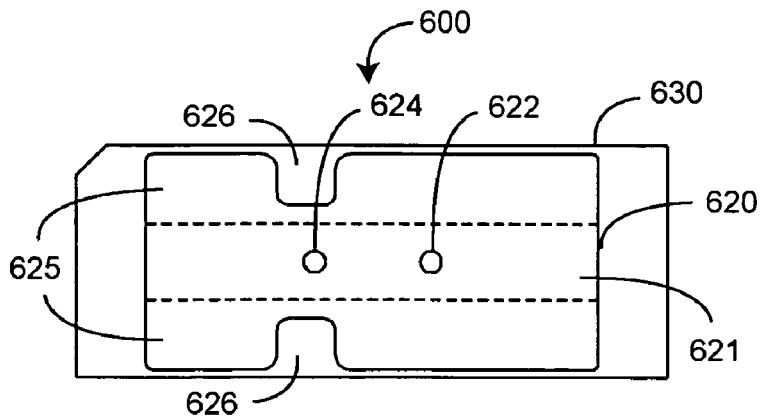
FIGS. 6A-D are top plan views of a tape assembly.

FIGS. 6A-D illustrate a tape assembly 600 having a face tape 610, a trifold wrap 620 and a release liner 630. As shown in FIG. 6A, the trifold wrap 620 has a center portion 621 disposed between foldable side portions 625, which are symmetrical about the center portion 621. The center portion 621 has an emitter aperture 622 and a detector aperture 624. The emitter aperture 622 passes light from the emitter 310 (FIG. 6B) and the detector aperture 624 passes light to the detector 350 (not visible). The side portions 625 have cutouts 626 configured to accommodate the housing 700 when the side portions 625 are folded. The trifold wrap 620 has a pressure sensitive adhesive (PSA) on the component side and a Med 3044 adhesive on the center portion 621 of the patient side. The release liner 630 is removably attached to the patient side of the trifold wrap 620.

Figure 6B:
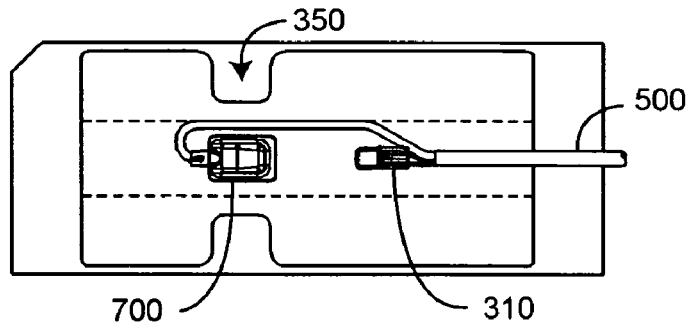
Figure 6C:
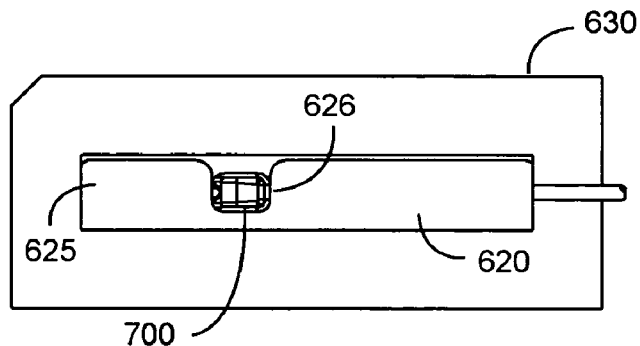
Figure 6D:
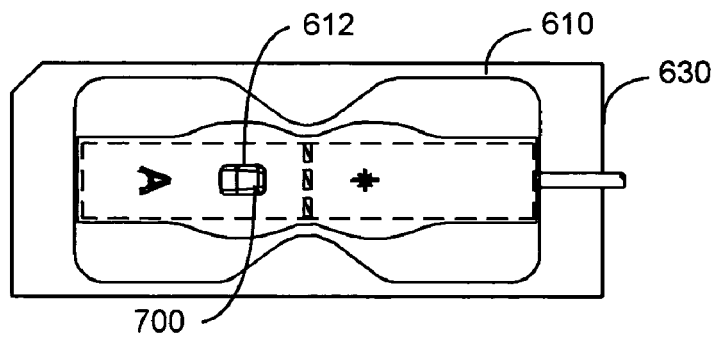
Figure 7A:
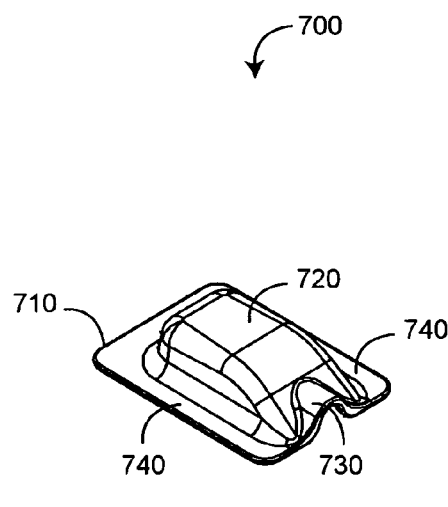
Figure 7B:
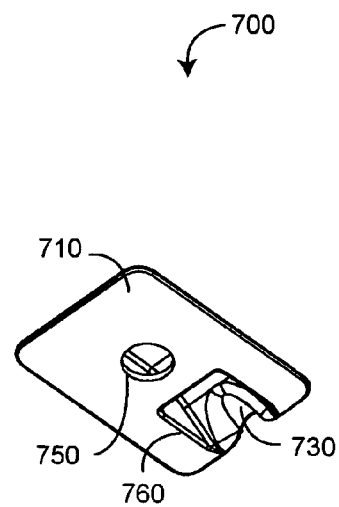

As shown in FIG. 6B, the housing assembly 500 is attached to the center portion 621 on the side opposite the release liner 630 so that the emitter 310 is aligned with the emitter aperture 622 and the housing aperture 750 (FIG. 5B) is aligned with the detector aperture 624. As shown in FIG. 6C, the side portions 625 are folded around the housing assembly 500 so that the housing 700 protrudes through the cutouts 626. As shown in FIG. 6D, the face tape 610 is fixedly attached to the trifold wrap 620 and removably attached to the release liner 630. A face tape aperture 612 also accommodates the protruding housing 700. In one embodiment, the trifold wrap 620 is polypropylene and the face tape 610 is a laminate of Bioflex RX848P and 3M 1527ENP.

FIGS. 7A-H illustrate a housing 700 that advantageously functions as both a light barrier and an optical cavity and is flexible and easy to manufacture. In one embodiment, the housing is injection molded as single piece of opaque, gray, medical grade PVC. As shown in FIGS. 7A-H, the housing 700 has a base 710, a cover 720, a cable strain relief 730, and a flange portion 740 of the base 710 disposed around the periphery of the cover 720. The cover 720 defines a pocket 770, which receives the detector assembly 400 (FIGS. 4A-F), as described above with respect to FIGS. 5A-B. The base 710 defines a generally centered, generally circular aperture 750 and an opening 760 for the pocket 770. The flange 740 provides a structure for securing the housing 700 to the trifold wrap 620 (FIGS. 6A-D). The pocket 770 is raised above the base 710, which advantageously recesses the detector 350 (FIG. 2) to reduce ambient and piped light from entering the detector 350 (FIG. 2) from the sides. In particular, the aperture 750 provides an optical cavity that allows optical radiation from the emitter 310 (FIG. 2) that propagates through the tissue site to reach the detector 350 (FIG. 2), while rejecting optical noise sources.

Further shown in FIGS. 7A-H, the housing 700 has a width 712, a length 714, a cover thickness 702, a side angle 772, a front angle 724 and a back angle 726. In one embodiment, the width 712 is about 0.44 inches, the length 714 is about 0.598 inches, the cover thickness 702 is about 0.02 inches, the side angle 722 is about 5°, the front angle 724 is about 10° and the back angle 726 is about 52.5°. Further, the aperture diameter 752 is about 0.117 inches, the pocket width 762 is about 0.2 inches and the cover height 728 is about 0.14 inches.

A pulse oximetry sensor has been disclosed in detail in connection with various embodiments. These embodiments are disclosed by way of examples only and are not to limit the scope of the claims that follow. One of ordinary skill in art will appreciate many variations and modifications.

What is claimed is:

1. A pulse oximetry sensor comprising:
    an emitter adapted to transmit optical radiation of at least two wavelengths into a tissue site;
    a detector adapted to receive optical radiation from said emitter after tissue site absorption;
    a tape assembly adapted to attach said emitter and said detector to said tissue site; and
    a flexible housing defining a pocket, said pocket configured to position and optically shield said detector.

2. The pulse oximetry sensor according to claim 1 wherein said housing comprises:
    a base; and
    a cover extending from said base defining the pocket, said pocket being raised above said base.

3. The pulse oximetry sensor according to claim 2 wherein said housing further comprises an aperture defined by said base so as to form an optical cavity that allows light originating from said emitter and absorbed by said tissue site to reach said detector while rejecting optical noise.

4. The pulse oximetry sensor according to claim 2 wherein said housing further comprises an opening defined in said bases, said opening configured to allow said detector to insert into said pocket.

5. The pulse oximetry sensor according to claim 2 wherein said housing further comprises a flange disposed around the periphery of said cover.

6. The pulse oximetry sensor according to claim 2 wherein said housing further comprises a flange providing structure to secure said housing to said tape assembly.

7. The pulse oximetry sensor according to claim 1 further comprising a cable assembly adapted to provide electrical communications between a pulse oximetry monitor and said emitter and said detector, a strain relief portion of said housing configured for a cable portion of said cable assembly.

8. The pulse oximetry sensor according to claim 1 wherein said housing is molded from an opaque, gray, medical grade PVC.

9. A pulse oximetry sensor comprising:
a detector adapted to receive optical radiation from an emitter after absorption by pulsatile blood flowing within a tissue site;
a shielded detector assembly having an EMI shield at least partially covering said detector;
a housing assembly having a flexible housing at least partially covering said shielded detector assembly,wherein said housing defines a pocket configured to position and optically shield said detector; and
a tape assembly folded around said housing assembly and adapted to attach said detector and said emitter to said tissue site.

10. The pulse oximetry sensor according to claim 9 wherein said flexible housing comprises:
a base; and
a cover extending from said base defining said pocket, said pocket being raised above said base and retaining said shielded detector assembly, said base defining an opening for said pocket and a generally circular aperture extending to said pocket.

11. The pulse oximeter sensor according to claim 9 wherein said aperture aligns with a grid portion of said EMI shield.

12. The pulse oximetry sensor according to claim 9 wherein said flexible housing further comprises a flange that secures said flexible housing to said tape assembly.

13. The pulse oximetry sensor according to claim 9 wherein said tape assembly comprises a tri-fold wrap having cutouts configured to accommodate said flexible housing.

14. The pulse oximetry sensor according to claim 9 wherein said tape assembly further comprises a face tape having a face tape aperture configured to accommodate said flexible housing.

15. A pulse oximetry sensor method comprising the steps of:
providing an emitter adapted to transmit optical radiation of at least two wavelengths into a tissue site;
providing a detector adapted to receive optical radiation from said emitter after absorption by pulsatile blood flowing within said tissue site;
incorporating said emitter and said detector within a cable assembly adapted to provide electrical communications between said emitter and said detector and a monitor;
EMI shielding said detector so as to reduce electromagnetic noise;
optically shielding said EMI shielded detector with an opaque, flexible housing so as to reduce optical noise from ambient light and piped light by forming a pocket within said flexible housing and enclosing said EMI shielded detector into said pocket; and
disposing said cable assembly within a tape assembly adapted to attach said emitter and said detector to a tissue site.

16. The pulse oximetry sensor method according to claim 15 wherein said enclosing step comprises the substep of:
inserting said EMI shielded detector into said pocket through an opening in a base of said flexible housing.

17. The pulse oximetry sensor method according to claim 15 wherein said forming step comprises the substeps of:
raising said pocket above said base so as to recess said detector from said base; and
defining an aperture extending through said base to said pocket so as to allow optical radiation from said emitter that propagates through said tissue site to said aperture to reach said detector.

18. The pulse oximetry sensor method according to claim 17 wherein said enclosing step comprises the further substep of aligning a light sensitive area of said EMI shielded detector with said aperture.

19. The pulse oximetry sensor method according to claim 15 wherein said disposing step comprises the substep of securing a flange portion of said housing to said tape assembly.

20. A pulse oximetry sensor comprising:
an emitter adapted to transmit optical radiation of at least two wavelengths into a tissue site;
a detector adapted to receive optical radiation from said emitter after tissue site absorption;
a housing defining a pocket configured to position and optically shield said detector; and
a wrap including cutouts configured to accommodate said housing, including a component side having foldable sides configured to fold respectively around said housing to capture sensor components including said emitter, and including a patient side opposite said component side, a portion of said patient side configured to attach said emitter and said detector to said tissue site.

21. The pulse oximetry sensor according to claim 20, wherein said housing comprises a flexible housing.

22. The pulse oximetry sensor according to claim 20, wherein said wrap comprises a trifold wrap.

* * * * *

UNITED STATES PATENT AND TRADEMARK OFFICE
CERTIFICATE OF CORRECTION

PATENT NO. : 7,280,858 B2  Page 1 of 1
APPLICATION NO. : 11/029009
DATED : October 9, 2007
INVENTOR(S) : Ammar Al-Ali et al.

It is certified that error appears in the above-identified patent and that said Letters Patent is hereby corrected as shown below:

At column 5, line 8, in claim 4, please delete "bases," and insert -- base, --, therefor.

At column 5, line 33-34 (Approx.), in claim 9, please delete "assembly-,wherein" and insert -- assembly, wherein --, therefor.

At column 5, line 45 (Approx.), in claim 10, please delete "a generally circular" and insert -- an --, therefor.

At column 5, line 47 (Approx.), in claim 11, please delete "claim 9" and insert -- claim 10 --, therefor.

Signed and Sealed this

Seventh Day of July, 2009

JOHN DOLL
*Acting Director of the United States Patent and Trademark Office*